United States Patent
Aston et al.

(10) Patent No.: US 7,186,267 B2
(45) Date of Patent: Mar. 6, 2007

(54) POROUS AND/OR POLYCRYSTALLINE SILICON ORTHOPAEDIC IMPLANT

(75) Inventors: Roger Aston, Malvern (GB); Leigh T Canham, Malvern (GB)

(73) Assignee: pSiMedica Limited, Worcestershire (GB)

( * ) Notice: Subject to any disclaimer, the term of this patent is extended or adjusted under 35 U.S.C. 154(b) by 447 days.

(21) Appl. No.: 10/297,803

(22) PCT Filed: Jun. 8, 2001

(86) PCT No.: PCT/GB01/02524

§ 371 (c)(1), (2), (4) Date: Jan. 23, 2003

(87) PCT Pub. No.: WO01/95952

PCT Pub. Date: Dec. 20, 2001

(65) Prior Publication Data

US 2004/0010313 A1    Jan. 15, 2004

(30) Foreign Application Priority Data

Jun. 10, 2000  (GB)  .................. 0014079

(51) Int. Cl.
*A61F 2/28* (2006.01)
(52) U.S. Cl. ................................. 623/16.11
(58) Field of Classification Search ........ 623/17.11, 623/23.72, 11.11, 16.11, 23.5, 23.51, 23.56, 623/23.57, 23.63; 424/423

See application file for complete search history.

(56) References Cited

U.S. PATENT DOCUMENTS

| | | | | |
|---|---|---|---|---|
| 3,893,196 A | * | 7/1975 | Hochman | .............. 424/422 |
| 3,960,786 A | * | 6/1976 | Akiyama | .............. 521/154 |
| 4,377,010 A | * | 3/1983 | Fydelor et al. | .......... 623/1.49 |
| 4,475,972 A | * | 10/1984 | Wong | .................. 156/167 |
| 4,565,722 A | * | 1/1986 | Highgate et al. | ......... 428/36.9 |
| 4,623,355 A | | 11/1986 | Sawruk | |
| 4,636,218 A | * | 1/1987 | Fukuura et al. | .......... 623/18.11 |
| 4,957,509 A | * | 9/1990 | Tamari et al. | ............ 424/423 |
| 6,328,762 B1 | * | 12/2001 | Anderson et al. | ........ 623/1.41 |
| 6,447,448 B1 | * | 9/2002 | Ishikawa et al. | ........ 600/300 |

FOREIGN PATENT DOCUMENTS

| | | |
|---|---|---|
| GB | 2 025 238 A | 1/1980 |
| WO | 99/53898 | 10/1999 |
| WO | 00/66190 | 11/2000 |

OTHER PUBLICATIONS

Canham et al; "Silicon as an Active Biomaterial"; Mat. Res. Soc. Symp. Proc., vol. 452, 1997; Materials Research Society; pp. 579-589.

Canham et al, "Silicon as an Active Biomaterial", Mat. Res. Soc. Symp. Proc. vol. 452, 1997, pp. 579-589.

* cited by examiner

*Primary Examiner*—Eduardo C. Robert
*Assistant Examiner*—David Comstock
(74) *Attorney, Agent, or Firm*—Nixon & Vanderhye P.C.

(57) ABSTRACT

The invention relates to orthopaedic implant materials and devices comprising porous and or polycrystalline silicon. Such materials and devices may be used in the treatment of one or more of the following conditions: hip fracture, arthrosis of the hip and knee, vertebral fracture, spinal fusion, long bone fracture, soft tissue repair, and osteoporosis.

2 Claims, 10 Drawing Sheets

LTC Stain etched scaffold HA deposit; 10keV SATW

LTC Polymer/PSi/Composite; Hole in HA layer; 20keV

Fig.2c.

LTC Polymer/PSi/Composite; Polymer only; 20keV

POROUS AND/OR POLYCRYSTALLINE SILICON ORTHOPAEDIC IMPLANT

This invention relates to new orthopaedic implant materials, to orthopaedic implant devices comprising said materials and to methods of fabrication of said materials and devices.

Orthopaedic implant materials are used for a range of applications relating to the fixation, fusion, reconstruction, treatment, and replacement of human and animal bones. Conditions treated in this way include bone fractures, bone degeneration, and bone cavities caused by events such as trauma, and infection.

Perhaps the most commonly used orthopaedic implant materials are titanium and stainless steel. For example these materials are used in the treatment of fractures; the fractured bone or bones being held together by screws and/or plates formed from the metal. Another material that has been used in bone fixation is self reinforced poly(glycolic acid) (SR-PGA). Screws formed from SR-PGA have been used in the treatment of cancellous bone fractures; an advantage of SR-PGA being its resorbability.

Bone replacements, such as joint replacements used in the treatment of arthrosis of the hip and knee, include orthopaedic implant material such as polymethylmethacrylate which is used as a bone cement in the replacement. Bone cavities resulting from such things as trauma and tumours are typically treated by autografting. However, the autograft harvest can result in considerable patient discomfort. For this reason work has been done to find an orthopaedic implant material that can act as a bone graft substitute. Materials such as collagen, hydroxylapatite, and tricalcium phophate have been used in treatment of such cavities.

The term "orthopaedic implant material" should not be confused with the term "bioactive material". For example GB 2317885 discloses certain types of porous silicon and polycrystalline silicon that are bioactive and that are capable of bonding to bone. Orthopaedic material is distinguished over bioactive material in that it must satisfy significantly more rigorous criteria. For a material to be bioactive it must simply bond to human or animal tissue. For a material to be suitable for orthopaedic implantation it must have an array of properties relating to its use in the treatment, repair, or replacement of bone.

If an orthopaedic implant material is used in the fabrication of an implant that is to be bonded to a bone, then good integration between the material and the bone may prevent loosening of the implant. Such loosening can be caused by infection or by reaction to the presence of the implant in the patient's body. For many applications it is therefore advantageous that the implant material should minimise the risk of such infection or adverse reaction. The risk of loosening can also be reduced by encouraging the bonding or growth of bone and supporting soft tissue to or into the implant.

Orthopaedic implant material often has to be strong, for example in the treatment of load bearing bones, and yet have a structure that allows the patient's own bone to grow and mature. This last factor is of particular importance in the treatment of young patients whose bones are continuing to grow. The mechanical properties of the implant materials are also important in maintaining the properties of the bone with which the material is associated. If the elastic modulus of the material differs from that of the bone, then the load experienced by the bone may be reduced. The phenomenon is known as stress shielding and is undesirable because living bone must be under a certain amount of tensile load in order to remain healthy.

An orthopaedic implant material used in the repair of a bone, may only be required for the duration of the repair. The use of resorbable materials that are absorbed by a patient's body over a period of time may go some way to meet this requirement. By having an implant that is absorbed, expensive and time consuming surgery removing the implant may be avoided. A beneficial substance, such as an antimicrobial agent or bone growth factors may also be incorporated in the resorbable material to be released as the material corrodes. Despite these favourable properties, a number of problems have been found with the use of prior art resorbable materials. For example, implants comprising such material may fail due to degradation before sufficient healing has occurred, or small debris particles at the last stages of degradation may cause pain in the affected area. Also resorbable materials often lack the mechanical strength for use in load bearing applications.

The properties of the orthopaedic implant material will depend on the application for which it is to be used. Two further properties that may be significant are: X-ray absorption properties, and compatibility with bone. The orthopaedic implant material should not impair the health of the bone; for example certain bone cements have been found to cause death of the bone with attendant loss of mechanical strength. The growth and/or repair of a bones will typically be monitored by standard medical imaging techniques such as X-ray radiography. Prior art orthopaedic implant materials, particularly metals, have been found to interfere with such imaging; and resorbable polymers have a density and composition comparable with that of surrounding tissue, making it difficult to distinguish between the two.

The factors that affect whether a material meets the requirements for orthopaedic implantation are therefore complex. It is, however, an object of the present invention to provide orthopaedic implant materials and orthopaedic implant devices that better satisfy these requirements. It is a further object to provide methods of fabricating these materials and devices.

According to a first aspect the invention provides an orthopaedic implant material comprising porous and or polycrystalline silicon.

An orthopaedic implant material is a material that may be used in the treatment and/or repair and/or replacement of animal or human bone. The bone may require such treatment and/or repair and/or replacement as a result of damage, disease, or a genetic defect. The term "replacement" is intended, for the purposes of this specification, to include the growth of a bone or part of a bone that was not present in a patient's body. The orthopaedic implant material may be adapted for use within an animal or human. It may also be adapted for use outside an animal or human body. For example, bone repair could be performed outside a patient's body, the repaired bone or bones then being replaced in the patient by surgery. Orthopaedic implant materials may be used to fix bones or bone portions together, it may form part of a scaffold to encourage bone growth across a gap between bones or to encourage regrowth of a damaged bone, and it may be used as a shield to prevent ingrowth of soft tissue in the space between bones or bone portions.

The use of porous and/or polycrystalline silicon promotes calcification and hence bone bonding. The semiconductor properties of porous and/or polycrystalline silicon opens the way for electrical control of the treatment, repair, or replacement process.

Preferably the orthopaedic implant material has a structure and composition such that it is suitable for use in the treatment of one or more of the following conditions: hip fracture, arthrosis of the hip and knee, vertebral fracture, spinal fusion, long bone fracture, soft tissue repair, and osteoporosis.

Preferably the porous and/or polycrystalline silicon is resorbable porous and/or polycrystalline silicon.

The use of resorbable porous and or polycrystalline silicon is advantageous since it obviates the need for surgery to remove the orthopaedic implant material. The porous and/or polycrystalline silicon is corroded in the body during the replacement of the bone. Porous and/or polycrystalline silicon also has a high mechanical strength, relative to prior art resorbable polymers used as orthopaedic implant materials, and is therefore more suitable for load bearing applications. The corrosion properties of porous silicon may be tailored to those required for a particular implant by controlling the pore size of the material.

The use of resorbable silicon is advantageous since the corrosion of porous and/or polycrystalline silicon results in the formation of silicic acid, a chemical that has been shown to stimulate bone growth.

The orthopaedic implant material may have a structure and composition such that it has an elastic modulus between 160 GPa and 0.1 GPa. The orthopaedic implant material may have a structure and composition such that it has an elastic modulus between 30 GPa and 1 GPa.

The bones of animals and humans have a range of elastic modulii. For example the elastic modulus of human cortical bone is typically between 15 and 30 GPa, whilst that of cancellous human bone is typically between 0.01 and 2 GPa. Mesoporous silicon, prepared from p+ wafers, having a porosity of 60% has an elastic modulus of 20 GPa, comparable to that of cortical bone. Mesoporous silicon prepared from p+ wafers and having a porosity of greater than 90% has an elastic modulus of approximately 1 GPa, comparable to that of cancellous bone. An advantage of the use of porous silicon, in the fabrication of orthopaedic implant material, is that its elastic modulus may be controlled by altering its microstructure and porosity. Indeed the Young's modulus of porous silicon may vary (depending on its structure and composition) from less than 2 GPa to more than 50 GPa.

Advantageously the orthopaedic implant material further comprises a bone cement and/or a polymer.

Preferably the orthopaedic material comprises one or more of: a morphogenetic protein, an antimicrobial agent, a fluoride, a vitamin D metabolite, calcitonin, raloxifene, oestrogen, a hormone.

Advantageously the orthopaedic material comprises derivatised porous silicon. More advantageously the derivatised porous silicon comprises Si—C and/or Si—O—C bonding.

The use of derivatisation in connection with resorbable orthopaedic implant is of particular value. This is because derivatisation allows the corrosion properties of the porous silicon to be tailored to those required for the implant.

According to a second aspect the invention provides an orthopaedic implant device formed, at least partly, from an orthopaedic implant material comprising porous and/or polycrystalline silicon An orthopaedic implant device is a device that may be used in the treatment, and/or replacement, and/or the repair of bone in an animal or human patient.

The device may comprise a fixitor selected from one or more of: a pin, a nail, a screw, a plate, a staple, a tack, an anchor, and a fixation block.

Preferably the orthopaedic implant device has a structure and composition such that it is suitable for the fixation of human cortical bone fractures. More preferably the orthopaedic implant device has a structure and composition such that it is suitable for the treatment of one or more of: hip fracture, vertebral fracture, spinal damage, craniofacial damage, and long bone fracture.

The orthopaedic implant device may comprise a biasing means for electrically biasing at least part of the porous and/or polycrystalline silicon. The biasing means may comprise a means for generating current flow through the orthopaedic implant device. The biasing means may comprise a battery.

The fixitor may has a structure and composition such that it is suitable for fixation of soft tissue to bone.

Alternatively the fixitor may have a composition and structure such that it is suitable for use as a prosthetic device.

The porous and/or polycrystalline material may be arranged such that the surface of the orthopaedic device is at least partly formed from the porous and/or polycrystalline silicon.

The orthopaedic device may further comprise animal and/or human bone. The orthopaedic device may comprise autografted animal or human bone.

The orthopaedic device may have structure and composition such that the device substantially prevents the interposition of adjacent soft tissues during bone treatment, and/or, repair, and/or replacement. The orthopaedic device may comprise a scaffold that encourages bone repair or replacement. The scaffold may comprise collagen.

Advantageously the orthopaedic device comprises a micromachined component, the structure and composition of said micromachined component being such that interaction between the orthopaedic device and surrounding tissue and cells is enhanced relative to use of the device without the micromachined component.

According to a third aspect the invention provides a method of making an orthopaedic implant material comprising the steps: taking a body of silicon or silicon containing compound, and forming the silicon or silicon containing compound into porous and/or polycrystalline silicon suitable for the treatment, and/or repair, and/or replacement of human or animal bone.

According to a fourth aspect the invention provides a method of making an orthopaedic implant device comprising the steps: taking a body of porous and/or polycrystalline silicon, and forming at least part of a device, suitable for the treatment, and/or repair, and/or replacement of human or animal bone, from the porous and/or polycrystalline silicon.

For the purposes of this specification the term "bioactive substance" is a substance that, when in contact with an animal or human body, is capable of eliciting a bond between the substance and the living tissue of the animal or human.

Also for the purposes of this specification the term "bioinert substance" is a substance that, when in contact with an animal or human body, is substantially not capable of eliciting a bond between the substance and the living tissue of the animal or human.

According to a fifth aspect, the invention provides a use of silicon for the manufacture of a medicament for the treatment and/or replacement and/or repair and/or fixation and/or reconstruction of bone.

Preferably the silicon is selected from one or more of: bioactive silicon, resorbable silicon, biocompatible silicon, porous silicon, polycrystalline silicon, amorphous silicon, and bulk crystalline silicon.

The porous silicon may be derivatised porous silicon. The derivatised porous silcion may comprise a Si—C or a Si—O—C covalent link. The derivatised porous silicon may comprise a carbon chain.

According to a sixth aspect the the invention provides a method of treating and/or repairing and/or replacing and/or fixing and/or reconstructing bone comprising the steps:
(a) implanting silicon into a region of an animal or human body requiring treatment and/or replacement and/or repair and/or reconstruction and /or fixation of bone; and
(b) allowing bone to grow onto at least part of the surface of the silicon.

The silicon may be selected from one or more of: bioactive silicon, resorbable silicon, biocompatible silicon, porous silicon, polycrystalline silicon, amorphous silicon, and bulk crystalline silicon.

The porous silicon may be derivatised porous silicon. The derivatised porous silcion may comprise a Si—C bond or a Si—O—C covalent link. The derivatised porous silicon may comprise a carbon chain.

Step (b) May be Performed Prior to Step (a)

According to a seventh aspect the invention provides a method of treating and/or repairing and/or replacing and/or fixing and/or reconstructing bone comprising the steps:
(a) implanting silicon into a region of an animal or human body to assist with treatment and/or replacement and/or repair and/or reconstruction and /or fixation of bone; and
(b) allowing the silicon to resorb.

The silicon may be selected from one or more of: bioactive silicon, resorbable silicon, biocompatible silicon, porous silicon, polycrystalline silicon, amorphous silicon, bulk crystalline silicon, and porous amorphous silicon.

The porous silicon may be derivatised porous silicon. The derivatised porous silcion may comprise a Si—C bond or a Si—O—C covalent link. The derivatised porous silicon may comprise a carbon chain.

Step (b) May be Performed Prior to Step (a)

According to an eighth aspect the invention provides a silicon channel and/or cavity structure comprising at least one silicon channel and/or cavity, the or at least one of the silicon channels and/or cavities being at least partially formed from silicon; characterised in that the silicon has a structure and composition such that at least part of the internal surface of the or at least one of the channels and/or cavities is bioactive.

Although bioactive forms of silicon have been discovered, these prior art silicon structures have only been found to exhibit bioactivity on their external surfaces. For example, experiments have been conducted in which porous silicon wafers have been immersed in simulated body fluid (SBF). While deposition of hydroxyapatite, indicating that porous silicon is bioactive, occurred on the external surface, no deposition was found to have occurred on the internal surfaces of the pores. The absence of deposition within the pores of porous silicon is described in Adv. Mater. 8(10) p 847–849 (1996).

The silicon surface which defines at least part of the or at least one of the channels and/or cavities may itself be bioactive. The silicon surface which defines at least part of the or at least one of the channels and/or cavities may induce bioactivity in any substance that partly defines the or at least one of the channels and/or cavities.

Preferably the or at least one of the channels and/or cavities has a largest cross-sectional dimension between 100 µm and 30 mm. More preferably the or at least one of the channels and/or cavities has a largest cross-sectional dimension between 100 µm and 1000 µm. Yet more preferably the or at least one of the channels and/or cavities has a largest cross-sectional dimension between 100 and 250 µm.

The or at least one of the channels and/or cavities may have an average cross-sectional area between 10 000 µm² and 900 mm². The or at least one of the channels and/or cavities may have an average cross-sectional area between 10 000 µm² and $10^6$ µm². The or at least one of the channels and/or cavities may have an average cross-sectional area between 10 000 and 62 500 µm².

Advantageously the channel and/or cavity may have a length greater than 200 microns. More advantageously the channel and/or cavity may have a length greater than 1 mm.

It should be noted that the pores formed in porous silicon, in other words silicon that is obtainable by stain etching and/or anodisation, have dimensions in the range 1.5 nm to 15 microns.

The silicon surface that defines at least part of the or at least one of the channels and/or cavities may be formed from one or more of: bioactive silicon, resorbable silicon, biocompatible silicon, porous silicon, polycrystalline silicon, amorphous silicon, and bulk crystalline silicon.

For applications such as the treatment of human or animal bones, the growth of bone into the structure may be desirable, for example channels and/or cavities may be employed, into which the bone can grow. If the internal surface of each channel and/or cavity is bioactive, then growth of the bone into the structure may be encouraged. For example bone may grow from one side of the structure to the other through a channel that protects the space within the channel from ingrowth by surrounding soft tissue. In a further example a channel may be in the form of a slit in the surface of the structure, into which bone may grow to assist bonding of the bone to the structure. Channels formed in the interior of the silicon structure or in the surface of the structure may be interconnected to facilitate growth of the bone into the structure and/or bonding of the bone to the structure.

Preferably the silicon structure has a shape and composition such that it is suitable for use as a scaffold for bone in-growth.

The silicon structure may have a shape and composition such that it is suitable for use as one or more of: a pin, a nail, a screw, a plate, a staple, a tack, an anchor, and a fixation block.

Preferably the silicon channel and/or cavity structure forms part of a bone growth device which further comprises a biasing means for applying a bias to the silicon channel and/or cavity structure. More preferably the bone growth device comprises a means for applying a bias to at least part of the silicon from which the structure is at least partly formed.

Advantageously the silicon channel and/or cavity structure comprises at least one external opening formed in its external surface by the or more than one of the channels and/or cavities. More advantageously at least part of said bioactive internal surface is located at a depth of at least 10 microns, from the or one of the external openings. Yet more advantageously at least part of said bioactive internal surface is located at a depth of at least 100 microns, from the or one of the external openings.

According to a ninth aspect the invention provides a use of a silicon channel and/or cavity structure for the manufacture of a medicament for the treatment and/or repair and/or replacement and/or reconstruction and/or fixation of bone in an animal or human subject, the channel and/or cavity structure comprising at least one silicon channel and/or cavity, the or at least one of the silicon channels and/or cavities being at least partially formed from silicon; characterised in that the silicon has a structure and composition such that at least part of internal surface of the or at least one of the channels and/or cavities is bioactive.

According to a tenth aspect the invention provides a method of treating and/or repairing and/or replacing and/or fixing and/or reconstructing bone comprising the steps:
(a) implanting a silicon channel and/or cavity structure into a region of an animal or human body requiring treatment and/or replacement and/or repair and/or reconstruction and /or fixation of bone, the channel and/or cavity structure comprising at least one silicon channel and/or cavity, the or at least one of the channels and/or cavities being at least partially formed from silicon; and
(b) allowing bone to grow into at least part of the or at least one of the silicon channels and/or cavities;
wherein the silicon, from which the or at least one of the channels and/or cavities is at least partially formed, has a structure and composition such that at least part of internal surface of the or at least one of the channels and/or cavities is bioactive, thereby facilitating the growth of bone into the or at least one of the channels and/or cavities.

Step (b) may precede step (a).

According to an eleventh aspect the invention provides a silicon composite material comprising silicon and a carrier material, the carrier material and silicon being arranged in such a manner that at least part of the silicon is in contact with at least part of the carrier material, characterised in that the silicon and carrier material have a structure and composition such that at least part of the silicon induces bioactivity in at least part of the carrier material.

Preferably the silicon is selected from one or more of: bioactive silicon, resorbable silicon, biocompatible silicon, porous silicon, polycrystalline silicon, amorphous silicon, and bulk crystalline silicon.

The carrier material may have a structure and composition such that it is resorbable.

Many such materials are bioinert, in other words they do not promote the growth of bone and so are relatively unsuitable for use as an orthopaedic implant material. However such materials may have properties, such as mechanical and resorption properties, which would, were it not for their lack of bioactivity, would be of value for the treatment and/or replacement and/or repair and/or reconstruction and/ or fixation of bone. Therefore the potential ability of silicon to induce bioactivity in such bioinert materials would be advantageous for orthopaedic applications.

The carrier material may comprise an organic compound. The carrier material may comprise a polymer. The carrier material may comprise a plastic material. The carrier material may comprise a material that is bioinert. The carrier material may comprise a material, other than bulk crystalline silicon, that is bioinert.

The silicon composite material may form at least part of an orthopaedic implant material. The silicon composite material may form at least part of a bone cement.

The or at least one of the particles has a largest dimension between 100 nm and 1 mm.

Preferably the or at least one of the particles has a largest dimension less than 1 mm. More preferably the or at least one of the particles has a largest dimension less than 100 microns.

According to an twelfth aspect the invention provides a silicon composite material comprising silicon and a carrier material, the carrier material and silicon being arranged in such a manner that at least part of the silicon is in contact with at least part of the carrier material, characterised in that the silicon and carrier material have a structure and composition such that at least part of the silicon induces bioactivity in at least part of the carrier material.

According to a twelfth aspect the invention provides bioactive porous amorphous silicon.

Amorphous silicon may be porosified by standard techniques. For example amorphous silicon may porosified by anodisation in aqueous or ethanolic HF, or it may be porosified by stain etching.

Preferably the bioactive porous amorphous silicon has a porosity between 1% and 90%. More preferably the bioactiove porous amorphous silicon has a porosity between 10% and 70%.

A silicon structure comprising bioactive porous amorphous silicon.

Advantageously the silicon structure comprises bioactive porous amorphous silicon and one or more of: titanium and stainless steel.

Preferably the porous amorphous silicon forms at least part of an orthopaedic implant material.

Advantageously the porous amorphous silicon forms part of an orthopaedic implant device.

The orthopaedic implant device may comprise porous amorphous silicon and a metal. The orthopaedic implant device may comprise porous amorphous silicon and a bio-inert material. The porous amorphous silicon may be bioactive. The porous amorphous silicon may form at least part of the surface of the orthopaedic implant.

Prior art orthopaedic implants may comprise bioinert materials such as titanium or stainless steel. The use of orthopaedic implants comprising porous amorphous silicon may be of value for the treatment or reconstruction of bone since it is a relatively straight forward to coat metals and other materials with amorphous silicon. Porosification of the amorphous silicon formed at the surface of the implant may confer bioactivity to the implant, allowing to bond with bone or other living tissue.

According to a thirteenth aspect the invention provides porous amorphous silicon for use as a biomaterial.

For the purposes of this specification a biomaterial is here defined as a non-living material suitable for use in or on the surface of a living human or animal body. It is intended to interact with the biological environment into which it is introduced. Such biomaterials can be bio-inert, bioactive or resorbable, depending on their interaction with the living tissue of the human or animal body.

According to a fourteenth aspect the invention provides a use of porous amorphous silicon for the manufacture of a medicament for the treatment and/or replacement and/or repair and/or replacement and/or fixation of bone.

According to a fifteenth aspect the invention provides a method of treating and/or repairing and/or replacing and/or fixing and/or reconstructing bone comprising the steps:
(a) implanting porous amorphous silicon into a region of an animal or human body requiring treatment and/or replacement and/or repair and/or replacement and /or fixation of bone; and
(b) fixing the porous amorphous silicon or at least part of the silicon to bone.

According to a sixteenth aspect the invention provides biocompatible porous amorphous silicon.

For the purposes of this specification a "biocompatible material" is a material that is biologically acceptable for specific applications.

According to a seventeenth aspect the invention provides a use of silicon for the manufacture of a medicament for determining, by X-ray radiography, the progress of treatment and/or repair and/or replacement and/or reconstruction and/or fixation of bone by X-ray.

Preferably the silicon is selected from one or more of: bioactive silicon, resorbable silicon, biocompatible silicon, porous silicon, polycrystalline silicon, amorphous silicon, and bulk crystalline silicon.

According to an eighteenth aspect the invention provides a method of monitoring the treatment and/or repair and/or replacement and/or fixation and/or reconstruction of bone, comprising the steps:
 (a) implanting silicon into a region of an animal or human body requiring treatment and/or replacement and/or repair and/or replacement and /or fixation of bone; and
 (b) performing an X-ray radiological analysis of said region of animal or human.

Preferably the silicon is selected from one or more of: bioactive silicon, resorbable silicon, biocompatible silicon, porous silicon, polycrystalline silicon, amorphous silicon, and bulk crystalline silicon.

The X-ray opacity of silicon, and particularly of resorbable silicon may be of value in monitoring the repair of bone. As the silicon resorbs and is replaced by bone, so its X-ray image becomes progressively more faint.

According to a nineteenth aspect the invention provides resorbable porous amorphous silicon.

According to a twentieth aspect the invention provides the use of porous amorphous silicon for the manufacture of a medicament for the treatment and/or repair and/or replacement and/or fixation and/or reconstruction of bone.

Whilst many countries do not, yet, permit the patenting of methods of treatment of the human or animal body by surgery or therapy, there are some (e.g. USA) who do. In order for there to be no doubt about the Paris Convention priority entitlement to such an invention in those countries that do permit it, the invention also comprises the treatment, therapeutic or prophylactic, of a human or animal body by implanting an orthopaedic implant material and allowing the orthopaedic implant material to treat, and/or repair, and/or replace bone in the animal or human.

Embodiments of the invention will now be described by way of example, with reference to the accompanying drawings, in which:

FIG. 2*b*(i) and (ii) show SEM images of the surfaces of an orthopaedic implant material, comprising a porous silicon powder and a bioinert resorbable polymer, that has been immersed in simulated human body fluid for two weeks;

Figure 1A:
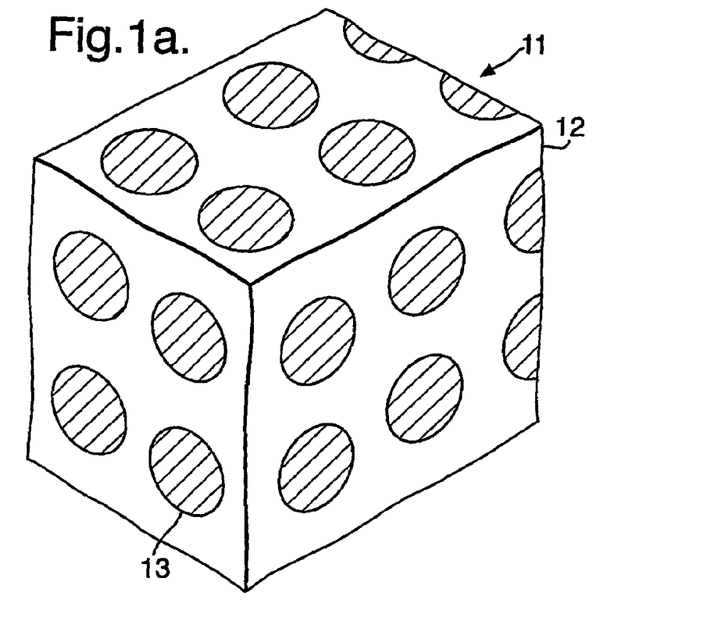
FIG. 1*a* shows a schematic diagram of part of an orthopaedic implant device, comprising a scaffold, according to the invention.
Figure 9:
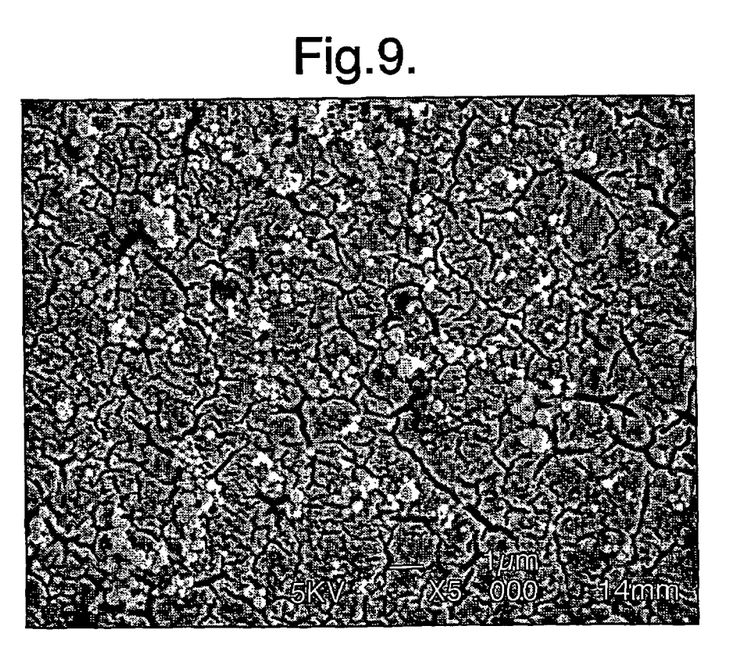

FIG. 9 shows an SEM image of a sample of porous amorphous silicon after immersion in SBF for a period of four weeks FIG. 1*a* shows a schematic diagram of part of an orthopaedic device, generally indicated by 11, according to the invention. The device comprises a silicon channel structure which is a scaffold for assisting in the repair of a damaged bone. The scaffold comprises mesoporous silicon 12 having a porosity of 60% to 90%, in which a multiplicity of channels 13 are formed. The channels occupy 65% of the volume of the scaffold. The channels 13 have diameters in the range 190 to 230 μm. The scaffold has a size and shape that approximates that of the missing bone to be replaced. The scaffold may be located in the region of the missing bone so that the surrounding bone may grow into the channels 13. As the growth occurs the mesoporous silicon 12 corrodes allowing the bone to be completely replaced. Alternatively the scaffold may be used to grow a patient's bone outside the body of the patient, the patient then being operated upon to replace the bone.

The scaffold may be fabricated by taking an ingot of bulk crystalline silicon and machining it to the desired shape. The channels 12 are then formed in the ingot by deep dry etching, sandblasting, focussed ion beam machining, or microdrilling. The technique adopted to form the channels will partly depend upon the size of the scaffold and on the dimensions of the channels 13. The shaped ingot is then anodised in an ethanoic acid HF solution for a period of 1 to 10 hours to render substantially the whole scaffold mesoporous.

Figure 1B:
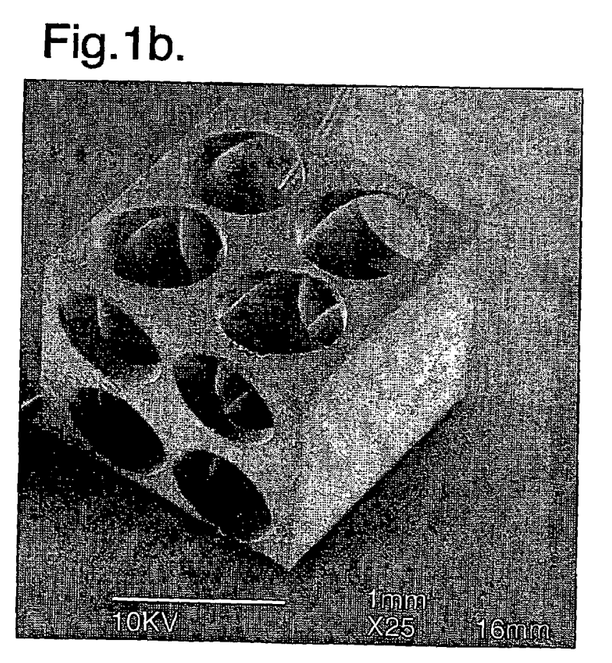
FIG. 1*b* shows an SEM image of a silicon structure.
Figure 1C:
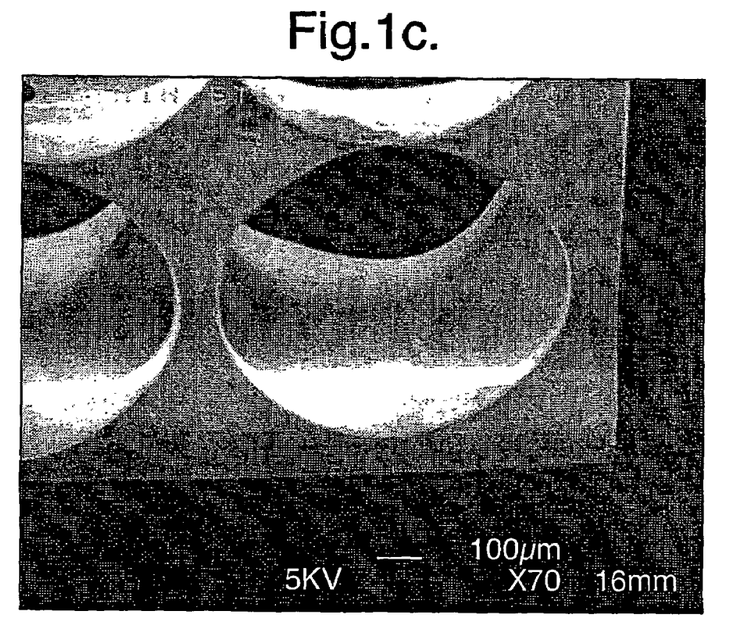
FIG. 1*c* shows an SEM image of a first prototype scaffold according to the invention.
Figure 1D:
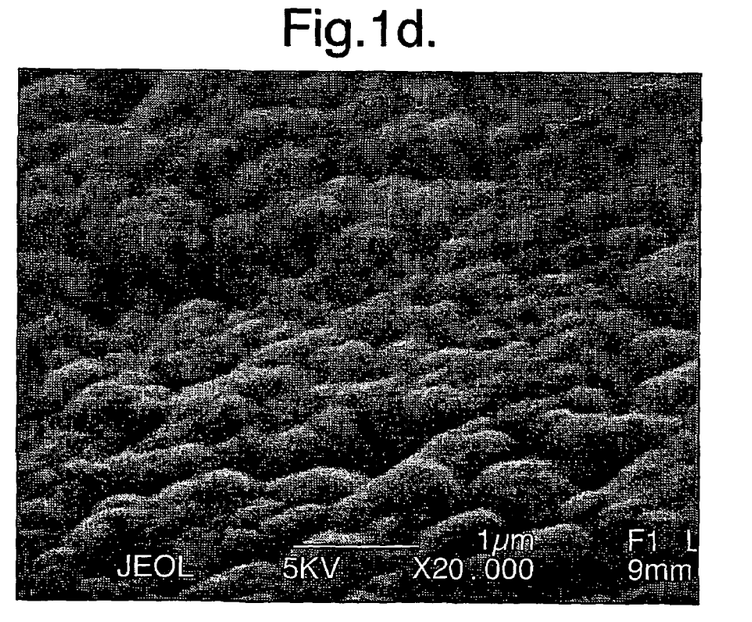
FIG. 1*d* shows an magnified SEM image of part of the first prototype scaffold shown in FIG. 1*c*.

FIG. 1*b* shows first prototype scaffold that comprises porous silicon. The first prototype scaffold, which is a silicon channel structure, was fabricated from a cube of single crystal silicon which was sawn out of a section of an ingot. The cube was then subjected to ultrasonic microdrilling to generate the structure shown in FIG. 1*b*. To remove mechanical damage due to the sawing and drilling operations, an isotropic chemical etch was performed on the structure shown in FIG. 1*b* (2 minutes in 25 ml $HNO_3$+5 ml HF+5 ml acetic acid). Finally, all surfaces were rendered mesoporous via stain etching (5 minutes in 50 ml of 40% HF and 1 ml of 70% $HNO_3$) to yield the FIG. 1*c* first prototype scaffold. The sidelength of the cube is between 1 and 2.5 mm, the channel diameter, for each channel drilled in the cube, is 0.8 mm. FIG. 1*d* shows the porous nature of the internal surface of the cavity shown in FIG. 1*c*.

Figure 1E:
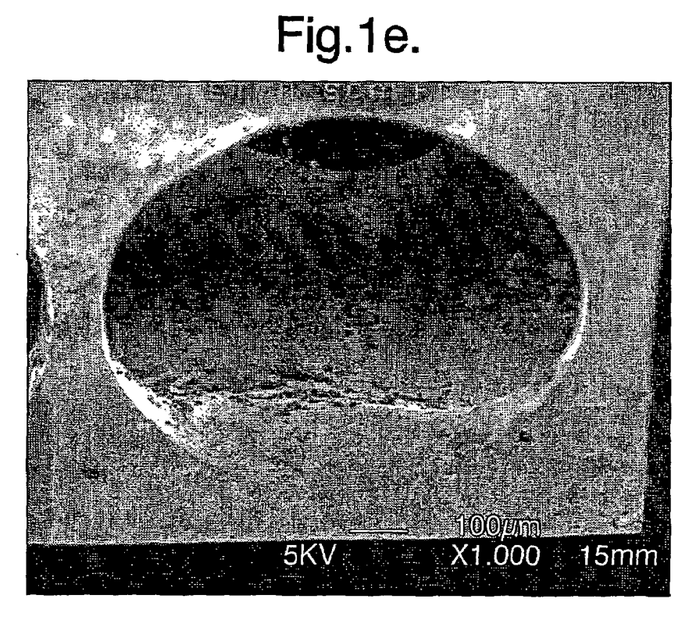
FIG. 1*e* shows an SEM image of the first prototype scaffold, to which a cathodic bias of approximately 5 volts has been applied, after it has been immersed in SBF for a period of approximately 10 hours.
Figure 1F:
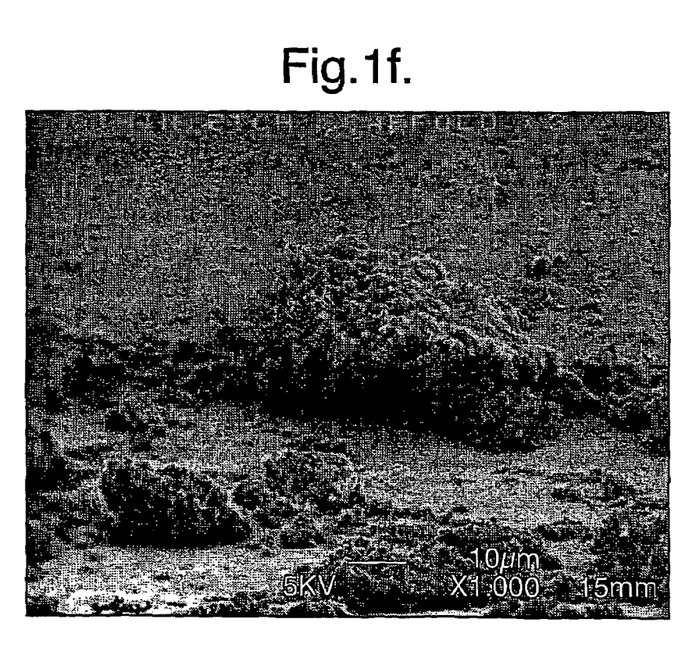
FIG. 1*f* shows a magnified SEM image of the scaffold surface shown in FIG. 1*e*.
Figure 1G:
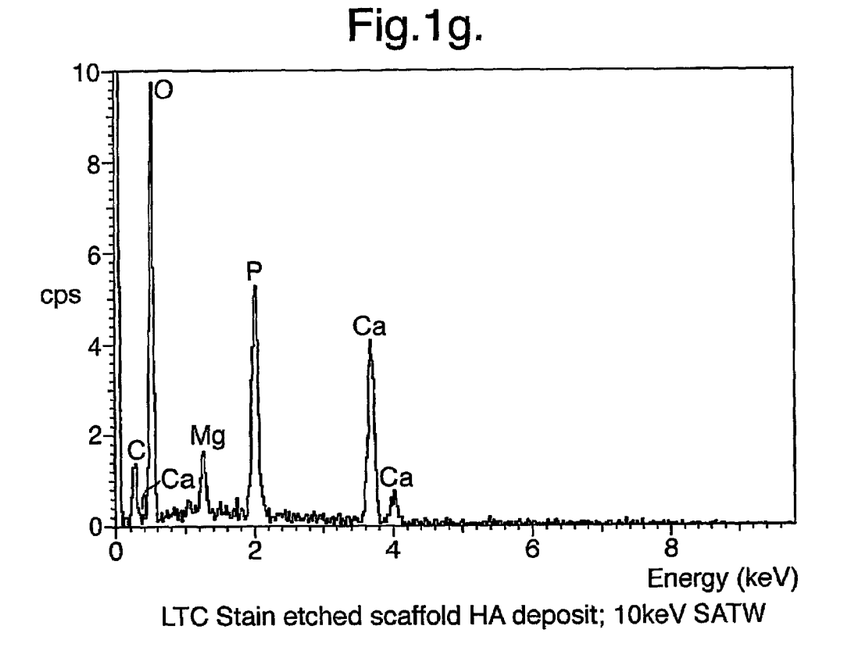
FIG. 1*g* shows an EDX plot for the hydroxyapatite coated surface of the structure shown in FIG. 1*e*.

The first prototype scaffold was then immersed in the meniscus of the SBF as described in WO 97/06101 with negative electrical bias applied by means of a gold wire. At a cathodic bias of 5 volts, an average electrical current of less than 6 mA flowed through the scaffold over a period of 10 hours. FIG. 1*e* shows the deposition of hydroxyapatite on the internal surface of the cavity shown in FIG. 1*e*, indicating that the internal surface of the scaffold is bioactive. FIG. 1*f* shows a magnified SEM image of the hydroxyapatite formed on the internal surface shown in FIG. 1*e*. FIG. 1*g* shows an EDX plot taken for part of the internal surface of the channel shown in FIG. 1*e*.

Figure 1H:
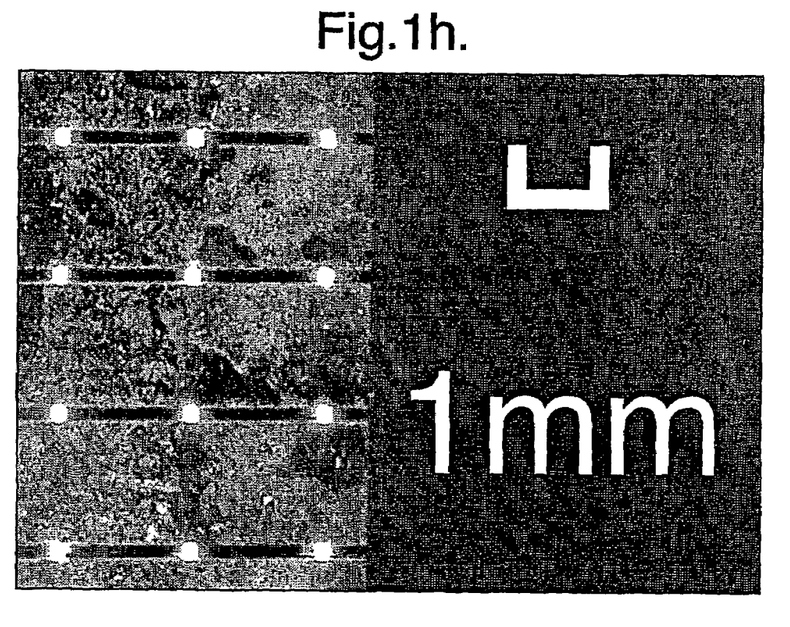
FIG. 1*h* shows an optical image of a silicon structure, after immersion in SBF.

FIG. 1*h* shows an optical image of a second prototype scaffold, which is a silicon channel structure according to the invention. To fabricate the second prototype scaffold square sections of sidelength 70 mm were sawn from standard 100 mm diameter circular wafers. Each square section was converted into a comb-like structure by sawing a series of parallel slits across the section, leaving a 2 mm strip undercut at the end of each slit to act as support. A 140 micron kerf blade with a pitch of 1.54 mm was used to define the 1.4 mm wide, 0.54 mm thick and 68 mm long silicon teeth.

A wood pile structure is then formed by stacking to the desired thickness a number of such sawn sections, with each being oriented orthogonal to its neighbours. The sections are bonded together either by conventional Si to Si wafer bonding techniques, by the use of biocompatible adhesives such as thin layers of calcium phosphate.

Figure 1I:
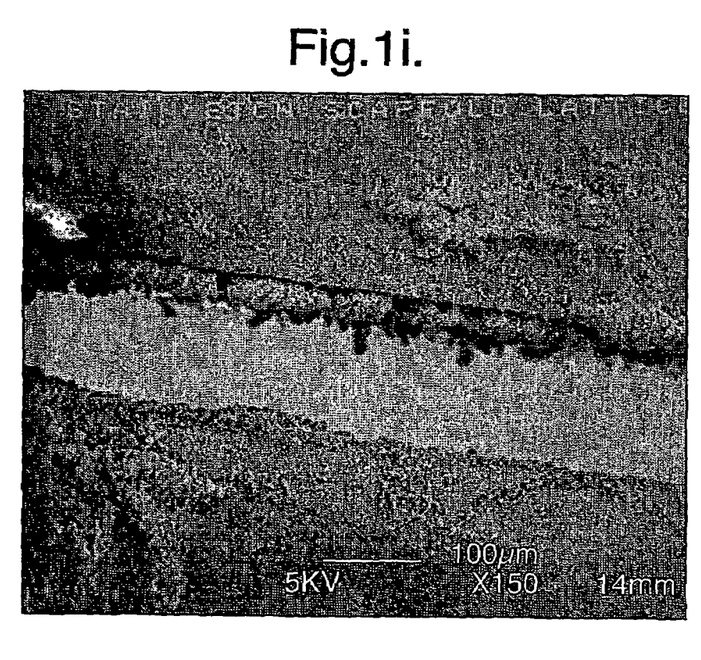
FIG. 1*i* shows an SEM image of part of the structure shown in FIG. 1*h* after the structure has been immersed in SBF.

The woodpile structure may then be porosified by standard stain etching or anodization techniques. FIG. 1*i* shows the formation of hydroxyapatite on the surface of the second prototype scaffold as a result of cathodically biasing the scaffold under 10 mAcm$^{-2}$ for 30 minutes in SBF.

Figure 2A:
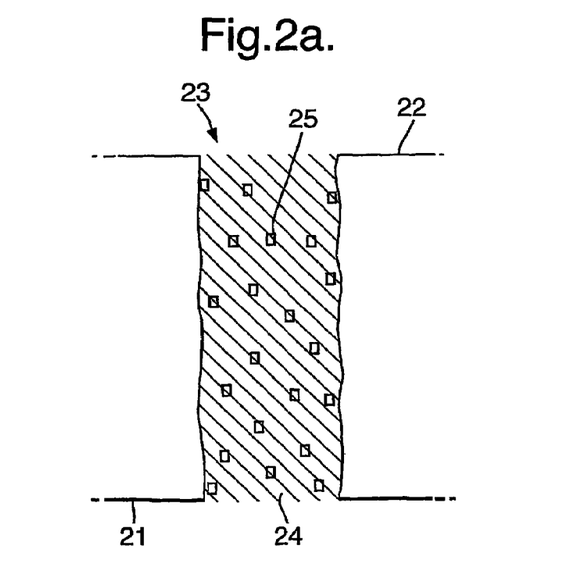
FIG. 2*a* shows a schematic diagram of an orthopaedic implant material according to the invention, comprising bone cement.
Figure 2B:
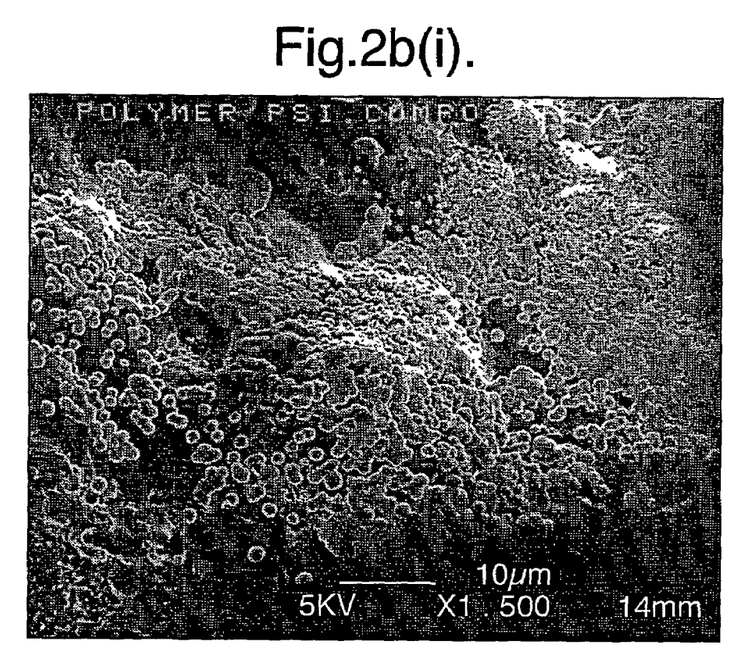

FIG. 2*a* shows a schematic diagram of two bone parts 21, 22 bonded together by a first orthopaedic implant material generally indicated by 23 according to the invention. The first implant material comprises a bone cement 24 and particles of porous silicon 25 dispersed in said cement 24. The porous silicon particles 25 are fabricated by anodisation of a number of wafers to form layers of porous silicon on the wafer surfaces. The porous silicon is detached, ultrasonically, from the wafers and the resulting powder is sieved to select diameters in the range 5 to 250 μm.

The sieved porous silicon particles 25 are then combined with calcium phosphate powder comprising 63% α-TCP (α-tricalcium phosphate), 28% DCP (dicalcium phosphate), 9% hydroxyapatite. The resulting silicon/phosphate powder may have a silicon content ranging from 5% to 80% depending on the application. The silicon/phosphate powder is combined with a 2.5% aqueous solution of NaHPO$_4$, the liquid to powder ratio being 0.32 cm$^3$ per gram of powder. (The percentage compositions for the aqueous solution, silicon, and phosphate powders are based on the weights of the components involved).

The combination of the aqueous solution with the silicon/phosphate powder results in the formation of a viscous paste that may be used to adhere the bone portions, before setting to form the required bond. The presence of the porous silicon particles 25 improves the mechanical strength of the material 23 and enhances bonding of the material 23 to the bone parts 21, 22.

FIG. 2*b* shows a SEM images of a second orthopaedic implant material. The material is a type of silicon composite material and comprises porous silicon particles and a polymer. The FIG. 2*b* image shows the composite after it has been immersed in SBF for a period of two weeks.

A p-type silicon wafer of 0.08 to 0.12 ohm cm resistivity was anodised in 20% ethanoic HF solution, electrolyte evaporation from the pores during air drying causes thick highly porous film to fragment and partially detach from the underlying bulk substrate. The wafer was inverted, tapped on its rear face, and approximately mm wide brown flakes of porous silicon collected onto underlying filter paper. These were then ground between two smooth glass plates into yellow porous silicon powder. 80 mg of polycaprolactone powder, a semicrystalline bioinert resorbable polymer, was mixed with 100 mg of porous silicon powder and the composite softened into a moldable form by heating it to 70 C. A 5 mm sphere was shaped by hand and then allowed to harden by slow cooling at room temperature to yield the second orthopaedic material. The silicon composite was then incubated in SBF for 2 weeks; FIG. 2*b* shows the SEM images of the second orthopaedic material after this incubation. The FIG. 2*b* images show growth of hydroxyapatite on the surface of the polymer coated silicon particles. The presence of the porous silicon particles has therefore conferred bioactivity to the formerly bioinert polymer.

Figure 2C:
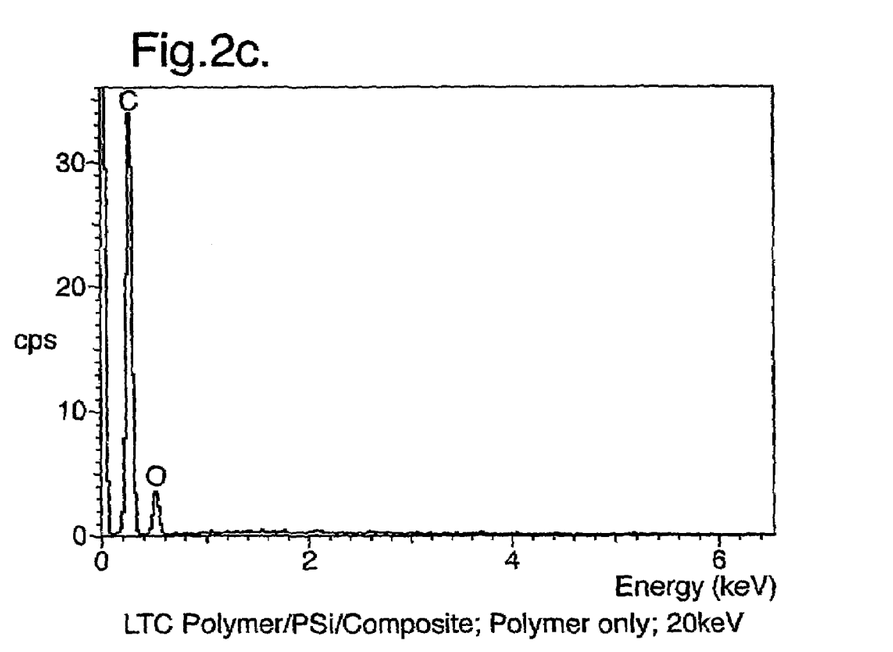
FIG. 2*c* shows an EDX plot for the bioinert resorbable polymer from which the FIG. 2*b* implant material was formed.

FIG. 2*c* shows an EDX plot for the polycaprolactone from which the second implant material shown in FIG. 2*b* is formed after immersion in simulated body fluid for two weeks. No silicon or hydroxyapatite is present and so only carbon and oxygen peaks are present on the plot.

Figure 2D:
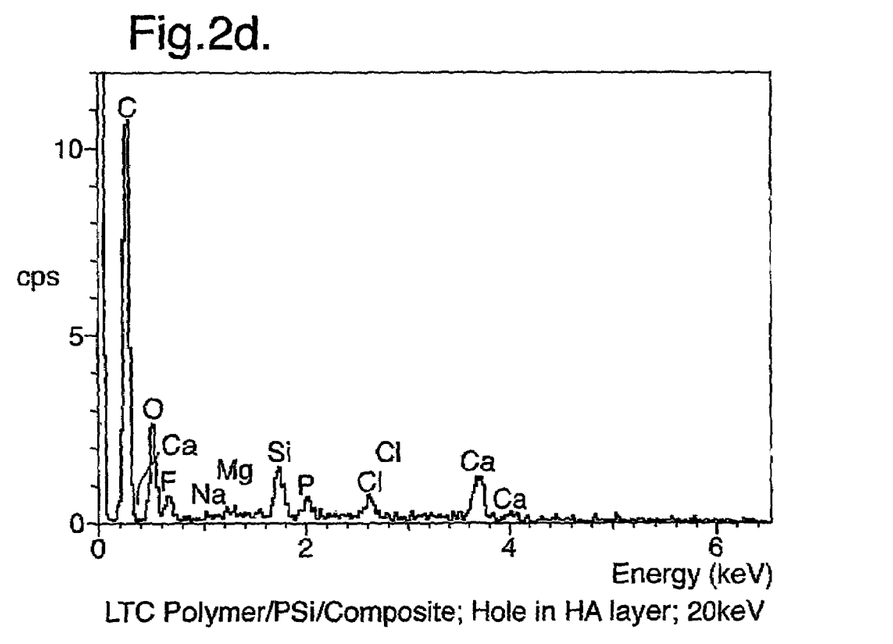
FIG. 2*d* shows an EDX plot for the implant material shown in FIG. 2*b*.

FIG. 2*d* shows an EDX plot for the second implant material after it has been immersed in simulated human body fluid for two weeks. The presence of silicon shows that both silicon and polymer are present, the other peaks are indicative of the presence of hydroxy apatite.

Figure 3:
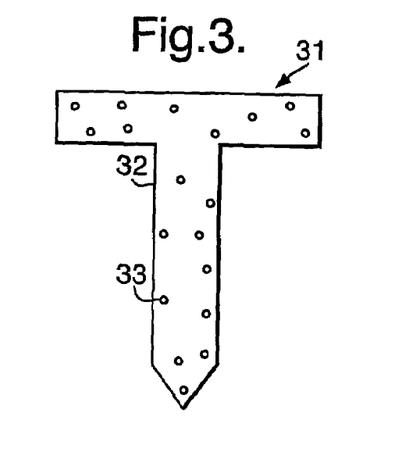
FIG. 3 shows a schematic diagram of an orthopaedic implant device, comprising a fixitor, according to the invention.

FIG. 3 shows a schematic diagram of an orthopaedic device according to the invention. The device comprises a fixitor, generally indicated by 31, formed from a resorbable polymer 32, such as polylactide co glycolide (PLGA), and mesoporous silicon powder 33. The device is suitable for fixing soft tissue to bone.

The porous silicon may be dispersed throughout the body of the fixitor 31. The PLGA is ground in a water cooled hammer mill to produce a micronised powder of the PLGA. A porous silicon powder 33 may be formed by anodisation, ultrasonic treatment, and sieving as discussed above, in relation to fabrication of bone cement. The PLGA and porous silicon powders are then thoroughly blended in proportions such that the resulting mixture has a 40 to 90% content, by mass, of silicon. The powder is compression molded at 12 MPa for 5 minutes at a temperature of approximately 85 C. to yield the fixitor. The presence of the porous silicon powder improves the mechanical properties of, and confers semiconducting properties to, the fixitor.

Alternatively the porous silicon may be dispersed substantially at the surface of the fixitor. A pure PLGA polymer is moulded to the shape of a fixitor and porous silicon particles are imbedded at pressures of 2 to 10 MPa and temperatures between 60 and 90 C. for 20 seconds to 2 minutes. The presence of porous silicon at the surface of the fixitor enhances its bioactivity and also confers semiconducting properties to its surface.

Figure 4:
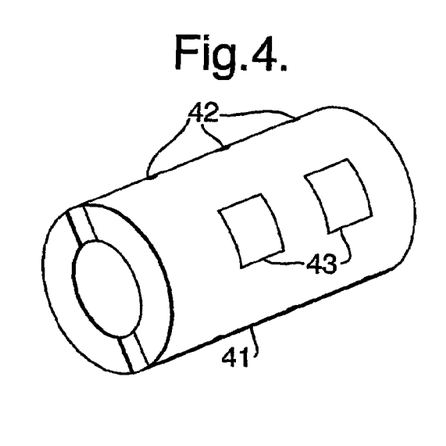
FIG. 4 shows a schematic diagram of an orthopaedic implant device, according to the invention, suitable for spinal fusion.

FIG. 4 shows a schematic diagram of an orthopaedic implant device, according to the invention, suitable for spinal fusion. The device comprises a cylinder 41 having a number of bone ingrowth slots 42 and vascularization openings 43. The cylinder 41 comprises bulk crystalline silicon and mesoporous silicon, the masoprosous silicon being formed on at least part of the surface of the cylinder 41. The length of the cylinder 41 is between 20 and 30 mm and its diameter is between 15 and 20 mm; the vascularisation openings 43 are approximately 6×7 mm and the bone ingrowth slots 42 are between 2 and 5 mm in diameter. The orientation of the device is such that the bone ingrowth slots 42 face the upper and lower vertebral ends.

A cylindrical ingot section, which may be p+ or n+ doped, is drilled and wet etched to remove a cylindrical core from its centre. The bone ingrowth slots 42 and the vascularisation openings 43 are mechanically drilled and given an HF:HNO$_3$ polish etch to remove saw damage. The entire cylinder 41 is then anodised using an ethanoic acid solution of HF yielding the orthopaedic device, suitable for spinal fusion, according to the invention. The bulk crystalline silicon, from which the cylinder 41 is principally formed, provides a high strength material suitable for this and other load bearing applications. For example, the tensile yield strength of bulk crystalline silicon is three times higher than that of stainless steel wire.

Figure 5:
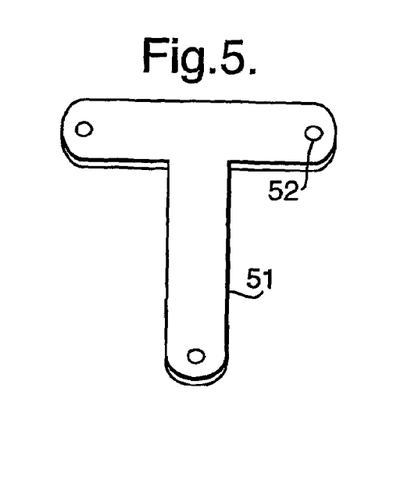
FIG. 5 shows a schematic diagram of an orthopaedic implant device, according to the invention, suitable for treatment of craniofacial damage.

FIG. 5 shows a schematic diagram of an orthopaedic implant device, according to the invention, suitable for treatment of craniofacial damage. The device comprises an osteosynthetic plate 51, which is fixed to the damaged bone to assist repair. The plate 51 is T-shaped, has a number of holes 52 drilled in it, and has two dimensions (corresponding to the arms and body of the T) in the range 25 to 30 mm; the third dimension being in the range 0.1 to 0.5 mm. The plate is fabricated by sawing a standard silicon wafer to form the T shape and drilling the required holes. Saw and drilling damage is removed by an isotropic wet etch step. The isotropic etch also results in rounding of the edges of the plate. The bulk crystalline silicon of the wafer is then anodised in ethanoic acid HF solution, either to form a layer of porous silicon at the surface of the plate 51 or to completely porosify the plate 51. (Complete porosification opening the way for complete corrosion of the plate, partial porosification enhancing bioactivity).

Experiments were performed to determine the X-ray properties of porous silicon. Images were recorded on polaroid film using an M Series Todd Research X-Ray unit. This X-ray fluoroscope has a large capacity drawer type examination chamber for viewing objects up to a maximum size of 64×46×16 cm. The X-ray tube has an operating voltage of 50–100 kV, an output current of 5 mA, a focal spot of 2 mm and a target angle of 20 degrees. Images were taken of various silicon structures, embedded within the legs of chicken cadavers, using an 80 kV operating mode with exposure times between 1 and 3 seconds. The polaroid film was placed on top of the object under view, the X-ray illuminating beam emerging from below the viewing chamber, towards the fluoresecnt screen above. Materials were embedded in the leg following incision with a scalpel blade.

Figure 6:
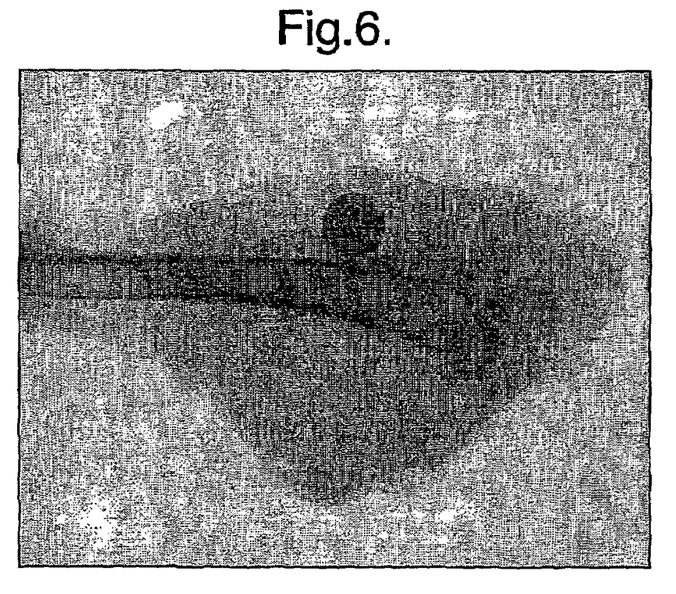
FIG. 6 shows an X-ray radiograph showing the absorption properties of a silicon disc.

FIG. 6 shows a radiograph comparing the X-ray absorption of a silicon disc with that of a titanium disc. Both the soft tissue, and the bony structures of the leg are evident; the distinct patella of the knee on the right hand side of the image, where the thin fibula is also distinguished from the thicker tibia bone. Both these bones extend to the ankle region beyond the left side of the image. The central dark circular region above the tibia corresponds to the titanium disc; the second circular image to the left of the titanium disc is that of the silicon disc.

Figure 7:
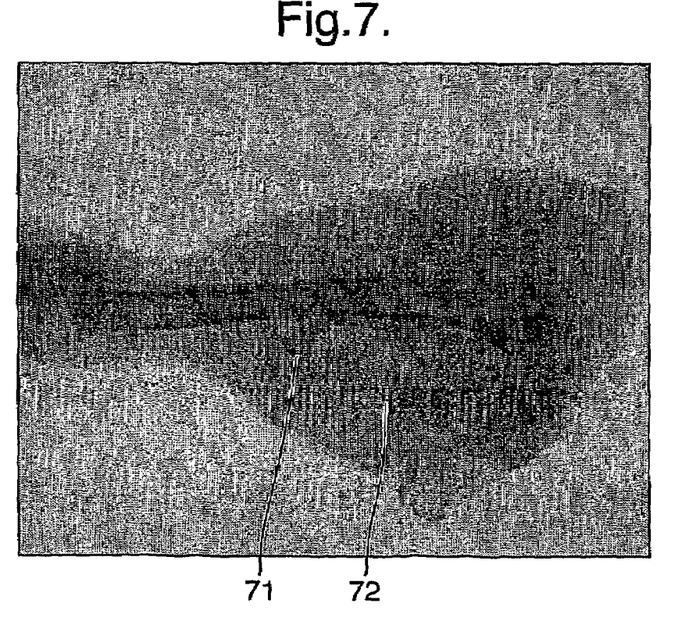
FIG. 7 shows an X-ray radiograph showing the absorption properties of a composite material comprising a bioinert resorbable polymer and porous silicon particles.

FIG. 7 shows an X-ray radiograph of a composite particle 71 of the second orthopaedic implant material, the fabrication of which was described earlier. The composite particle lies at one end of an incision that extends from position 71 to position 72. The incision forms a pale line between these two points on the radiograph. A particle of polymer, having approximately the same size as the composite particle 71 was placed at position 72 before the radiograph was taken, and as can be seen, does not form any image. The presence of the porous silicon therefore confers X-ray opacity to the composite.

Prior art orthopaedic implants often comprise a bioinert metal such as stainless steel. An orthopaedic implant according to the invention may comprise stainless steel and porous amorphous silicon. At least part of the surface of the implant may be formed by the porous amorphous silicon.

Device quality amorphous silicon may be deposited on stainless steel by standard techniques such as that described in Physical Review Letters Vol. 77, p 1885–1888 (1996). Silane is decomposed using an rf plasma at 250 C., and boron doped via the addition of diborane gas, to yield a 2 micron thick film of amorphous silicon. The substrate onto which the amorphous silicon is deposited is an optically polished stainless steel plate.

Once the amorphous silicon has been deposited it may be porosified, again by standard techniques such as those described in EP 96925906.8. Circular regions of the plate are selectively anodized in HF solution (HF/water/ethanol:5/9/6 by volume).

Figure 8:
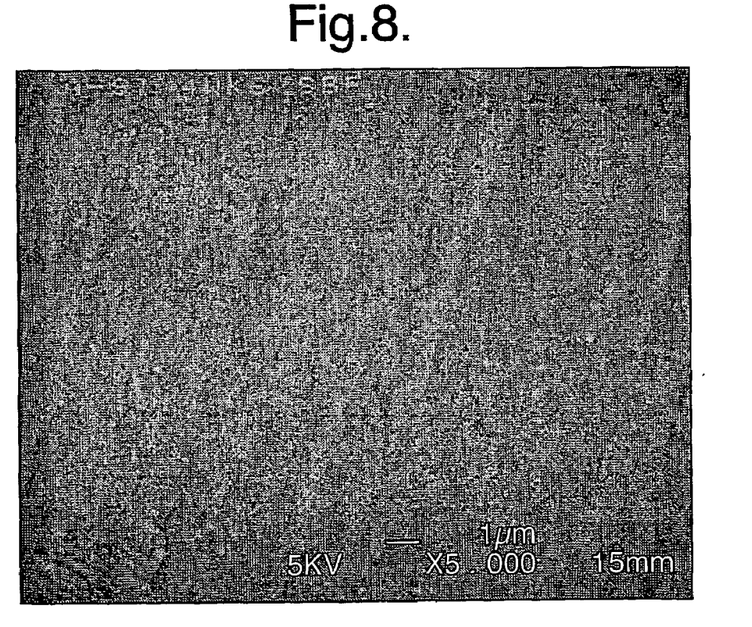
FIG. 8 shows an SEM image of a sample of amorphous silicon after immersion in simulated body fluid (SBF) for a period of 4 weeks.

The plate was incubated in simulated body fluid (SBF) for approximately 4 weeks, the solution being replaced by fresh simulated body fluid after 2 weeks. FIG. 8 shows an SEM image of a sample of amorphous silicon that has been deposited on a stainless steel plate, and FIG. 9 shows a sample of amorphous porous silicon, formed on a different part of the same steel plate. Both the FIGS. 8 and 9 SEM images are for surfaces that have been immersed in SBF for the four week period. The FIG. 8 image shows that substantially no hydroxyapatite has deposited on the non-porous amorphous silicon substrate. There is also no evidence of corrosion.

FIG. 8 contrasts with FIG. 9 in that both hydroxyapatite deposition and corrosion has occurred as a result of treatment with SBF. The corrosion of the surface indicates that the amorphous porous silicon is resorbable and the deposition of the hydroxyapatite indicates that the amorphous porous silicon is bioactive and biocompatible.

The invention claimed is:

1. A method of treatment, repair, or replacement of human or animal bone, comprising:
   (a) preparing a semiconductor porous and/or polycrystalline silicon and a carrier material to form a silicon composite material such that at least part of the silicon is in contact with at least part of the carrier material;
   (b) implanting the silicon composite material; and
   (c) allowing the bone to bond to the silicon composite material;
   wherein the silicon and carrier material have a structure and composition such that at least part of the silicon induces bioactivity in at least part of the carrier material.

2. A method of treatment, repair, or replacement of human or animal bone, comprising:
   (a) preparing a semiconductor porous and/or polycrystalline silicon and a resorbable carrier material to form a silicon composite material such that at least part of the silicon is in contact with at least part of the carrier material;

(b) implanting the silicon composite material; and
(c) allowing the bone to bond to the silicon composite material;

wherein the carrier material has a structure and composition such that it is resorbable and wherein the silicon and resorbable carrier material have a structure and composition such that at least part of the silicon induces bioactivity in at least part of the carrier material.

* * * * *